US009452101B2

(12) United States Patent
Tomlinson et al.

(10) Patent No.: US 9,452,101 B2
(45) Date of Patent: Sep. 27, 2016

(54) NON-INVASIVE, VIBROTACTILE MEDICAL DEVICE TO RESTORE NORMAL GAIT FOR PATIENTS SUFFERING FROM PERIPHERAL NEUROPATHY

(75) Inventors: Blain Tomlinson, Long Beach, CA (US); David Eckhous, Long Beach, CA (US); Daniel B. Edney, Orange, CA (US); Royce Rumsey, Laguna Beach, CA (US)

(73) Assignee: WALKJOY, INC., Long Beach, CA (US)

( * ) Notice: Subject to any disclaimer, the term of this patent is extended or adjusted under 35 U.S.C. 154(b) by 532 days.

(21) Appl. No.: 13/442,650

(22) Filed: Apr. 9, 2012

(65) Prior Publication Data

US 2012/0259255 A1   Oct. 11, 2012

Related U.S. Application Data

(60) Provisional application No. 61/474,215, filed on Apr. 11, 2011.

(51) Int. Cl.
*A61H 3/00* (2006.01)
*A61H 23/02* (2006.01)
(Continued)

(52) U.S. Cl.
CPC .............. *A61H 3/00* (2013.01); *A61B 5/112* (2013.01); *A61H 23/0218* (2013.01); *A61H 39/007* (2013.01); *A61B 5/4836* (2013.01); *A61B 5/6828* (2013.01); *A61B 2562/0219* (2013.01); *A61H 2201/0184* (2013.01); *A61H 2201/5012* (2013.01); *A61H 2201/5015* (2013.01);

(Continued)

(58) Field of Classification Search
CPC .... A61H 3/00; A61H 23/0218; A61H 39/00; A61H 39/007
USPC .................... 601/5, 23, 33, 34, 46
See application file for complete search history.

(56) References Cited

U.S. PATENT DOCUMENTS 5,604,816 A * 2/1997 Totani ............... A61H 23/0236
                                                    381/396
6,872,187 B1 * 3/2005 Stark et al. .................... 602/16
(Continued)

FOREIGN PATENT DOCUMENTS

WO      2005094679      10/2005

OTHER PUBLICATIONS

PCT International Search Report; PCT US 12/32927; mailed Aug. 3, 2012; 8 pages.

(Continued)

*Primary Examiner* — Justine Yu
*Assistant Examiner* — Kathrynn Lyddane
(74) *Attorney, Agent, or Firm* — Setina Brunda Garred & Brucker

(57) ABSTRACT

Provided is a comfortable and discrete device wearable by a patient to restore balance and gait. The device re-establishes the sensorimotor loop by providing the patient with a secondary signal to healthy nerves around the knee to alert the patient that the patient's heel has just struck the ground. In this regard, the device monitors the patient's leg movements to detect when the patient's heel strikes the ground and sends the secondary signal, i.e., vibrotactile stimulation, in response to the detected heel strike. The central nervous system incorporates the new signal and the motor system responds as if there is not loss of sensation in the foot and returns to its normal gait.

20 Claims, 4 Drawing Sheets

(51) Int. Cl.
*A61B 5/11* (2006.01)
*A61H 39/00* (2006.01)
*A61B 5/00* (2006.01)

(52) U.S. Cl.
CPC .............. *A61H2201/5035* (2013.01); *A61H 2201/5069* (2013.01); *A61H 2201/5084* (2013.01); *A61H 2201/5097* (2013.01)

(56) References Cited

U.S. PATENT DOCUMENTS 7,191,644 B2    3/2007   Haselhurst et al.
8,040,223 B2 * 10/2011   Mortimer et al. ......... 340/407.1
2004/0173220 A1   9/2004   Harry et al.
2005/0131317 A1   6/2005   Oddsson et al.
2007/0173903 A1   7/2007   Goren
2007/0203533 A1 * 8/2007   Goren et al. .................... 607/49
2008/0077354 A1   3/2008   Ihashi
2009/0024065 A1 * 1/2009   Einarsson ....................... 602/26
2009/0143704 A1   6/2009   Bonneau et al.
2009/0177131 A1   7/2009   Dar et al.

OTHER PUBLICATIONS

Australian Government IP Australia; Patent Examination Report No. 1; Oct. 20, 2015; 4 pages.

* cited by examiner

NON-INVASIVE, VIBROTACTILE MEDICAL DEVICE TO RESTORE NORMAL GAIT FOR PATIENTS SUFFERING FROM PERIPHERAL NEUROPATHY

CROSS-REFERENCE TO RELATED APPLICATIONS

This application claims the benefit of U.S. Provisional Application No. 61/474,215, filed Apr. 11, 2011.

STATEMENT RE: FEDERALLY SPONSORED RESEARCH/DEVELOPMENT

Not Applicable

BACKGROUND

1. Field of the Invention

The present invention relates generally to a medical device for restoring gait in a patient, and more specifically to a non-invasive medical device that imparts a vibrotactile force on the patient's leg to provide proprioceptive feedback to the patient for purposes of restoring gait and balance.

2. Description of the Prior Art

Over 220 million people worldwide suffer from peripheral neuropathy, including 21 million Americans. Peripheral neuropathy affects nerves that carry information to and from the brain and spinal cord to the rest of the body. In over 10 million Americans, peripheral neuropathy results in a loss of sensation and an inability to control muscles, which in turn leads to poor gait, balance, increased falls and foot ulcers. In general, one third of the patients suffering from peripheral neuropathy are diabetics, one third are oncology patients, Auto Immune Disease Patients, Spinal Cord Injury patients, and the remaining one third are of unknown causes. Over 1.5 million new patients are typically diagnosed each year.

Peripheral neuropathy patients are 23 times more likely to fall and 6 times more likely to become chronic fallers. Falls account for approximately $26 billion in medical costs each year. Overall, peripheral neuropathy costs the United States healthcare system approximately $48 billion per year.

During normal human gait, transmission of cutaneous feedback from the feet is typically essential for maintaining normal gait and balance. Non-nociceptive cutaneous feedback from the feet is normally transduced via mechanoreceptors at the sole and transmitted via the afferent nerve fibers to the central nervous system.

In patients suffering from peripheral neuropathy, there is a functional loss of nerve fibers, which is usually irreversible and leads to gait and balance disorders. Another problem commonly associated with peripheral neuropathy is the increased risk of developing foot ulcerations. More specifically, the decrease in cutaneous feedback from the feet of diabetic patients suffering from peripheral neuropathy and the associated gait impairment may result in the development of abnormal planar pressure during human gait. Abnormal planar pressure results in abnormal repetitive stress to the feet and thus increases the risk of developing foot ulcerations.

As is apparent from the foregoing, there is a need in the art for an effective treatment for communicating sensory feedback to the patient's suffering from peripheral neuropathy and peripheral nerve damage so as to improve gait and balance in those patients. The present invention addresses this particular need, as will be discussed in more detail below.

BRIEF SUMMARY

There is provided a comfortable and discrete medical device wearable by a patient to restore balance and gait. The device is configured to re-establish the sensorimotor loop by providing the patient with a secondary signal to healthy nerves around the knee to alert the patient that the patient's heel has just struck the ground. In this regard, the device monitors the patient's leg movements to detect when the patient's heel strikes the ground and sends the secondary signal, i.e., vibrotactile stimulation, upon detection of the heel strike. The central nervous system incorporates the new signal and the motor system responds as if there is not loss of sensation in the foot and returns to its normal gait. In this regard, the device allows the patient to restore balance and gait without having to retrain motor control.

According to one embodiment, the medical device includes a housing configured to be wearable on a patient's leg. The device further includes a vibrating element connected to the housing such that at least a portion of the vibrating element is moveable through a housing opening to impart a vibration force upon the patient's leg. A control unit is connected to the housing and is in operative communication with the vibrating element. The control unit is configured to detect leg movements related to the patient's gait and to generate an actuation signal in response to detection of foot impact to actuate the vibrating element.

The control unit may measure rotation of the patient's leg during the patient's gait to detect foot impact. The control unit may also measure acceleration of the patient's leg during the patient's gait to detect foot impact. The control unit may include an accelerometer configured to detect acceleration along 1-3 axes. The control unit may be configured to detect leg movements according to one of a plurality of pre-programmed gait settings. The control unit may be configured to allow a user to selectively switch between the plurality of pre-programmed gait settings.

The housing may be configured to be positionable adjacent the tibia tubercle of the patient's leg during use.

The vibrating element may include a permanent magnet and a winding. The vibrating element may be configured to impart a vibrating force at approximately 250 Hz. The vibrating element may impart the vibrating force for approximately 10-200 ms. The vibrating element may be configured to define a rise time of approximately 10-40 ms.

The present invention is best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The detailed description set forth below is intended as a description of the presently preferred embodiment of the invention, and is not intended to represent the only form in which the present invention may be constructed or utilized. The description sets forth the functions and sequences of steps for constructing and operating the invention. It is to be understood, however, that the same or equivalent functions and sequences may be accomplished by different embodiments and that they are also intended to be encompassed within the scope of the invention.

Figure 1:
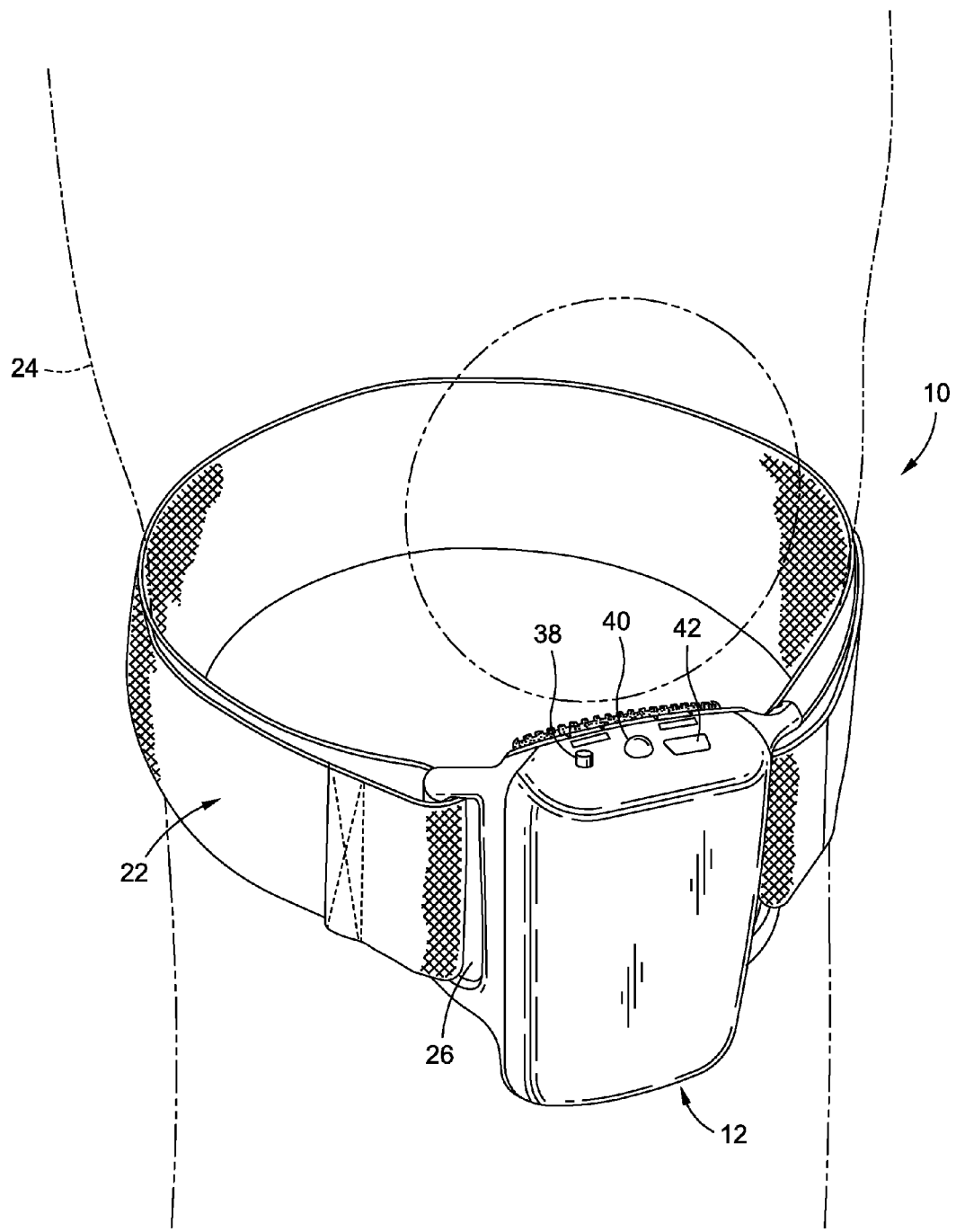
FIG. 1 is an upper perspective view of an embodiment of a gait restoring medical device shown on a patient's leg, wherein the patient's leg is shown in phantom.

Referring now to the drawings, wherein the showings are for purposes of illustrating a preferred embodiment of the present invention, and not for purposes of limiting the same, there is shown with initial reference to FIG. 1, a non-invasive, vibrotactile medical device 10 for restoring normal gait in patients suffering from peripheral neuropathy. In general, the device 10 is configured to impart vibrotactile stimulation on the patient's leg adjacent the tibia tubercle of the patient. The vibrotactile stimulation is intended to restore proprioception and kinesthesia by reeducating the Gamma Efferent Feedback Loop, which is typically diminished in peripheral neuropathy patients, as well as in patients suffering from other nerve impairment syndromes (i.e., PNS and CNS). The device 10 is also configured to monitor the leg movements related to the patient's gait and generate the vibrotactile stimulation pulse at a fixed specific point on the patient's gait cycle, such as during a detected heel strike. The stimulation is intended to compensate for loss of feeling in the patient's feet and to restore proprioception to the gait.

As used herein, the word "gait" is used to refer to the way locomotion is achieved using human limbs. Different gaits are characterized by differences in limb movement patterns, overall velocity, forces, kinetic and potential energy cycles, and changes in the contact with the surface (i.e., ground, floor, etc.).

The term "proprioception" is used herein to refer to the sense of the relative position of neighboring parts of the body to indicate whether the body is moving with the required effort, as well as to identify where the various parts of the body are located relative to each other.

Furthermore, the term "kinesthesia" refers to the awareness of the position and movement of the parts of the body by means of sensory organs (proprioceptors) in the muscles and joints, which is used to help a person stay balanced and coordinate his or her movements.

Figure 2:
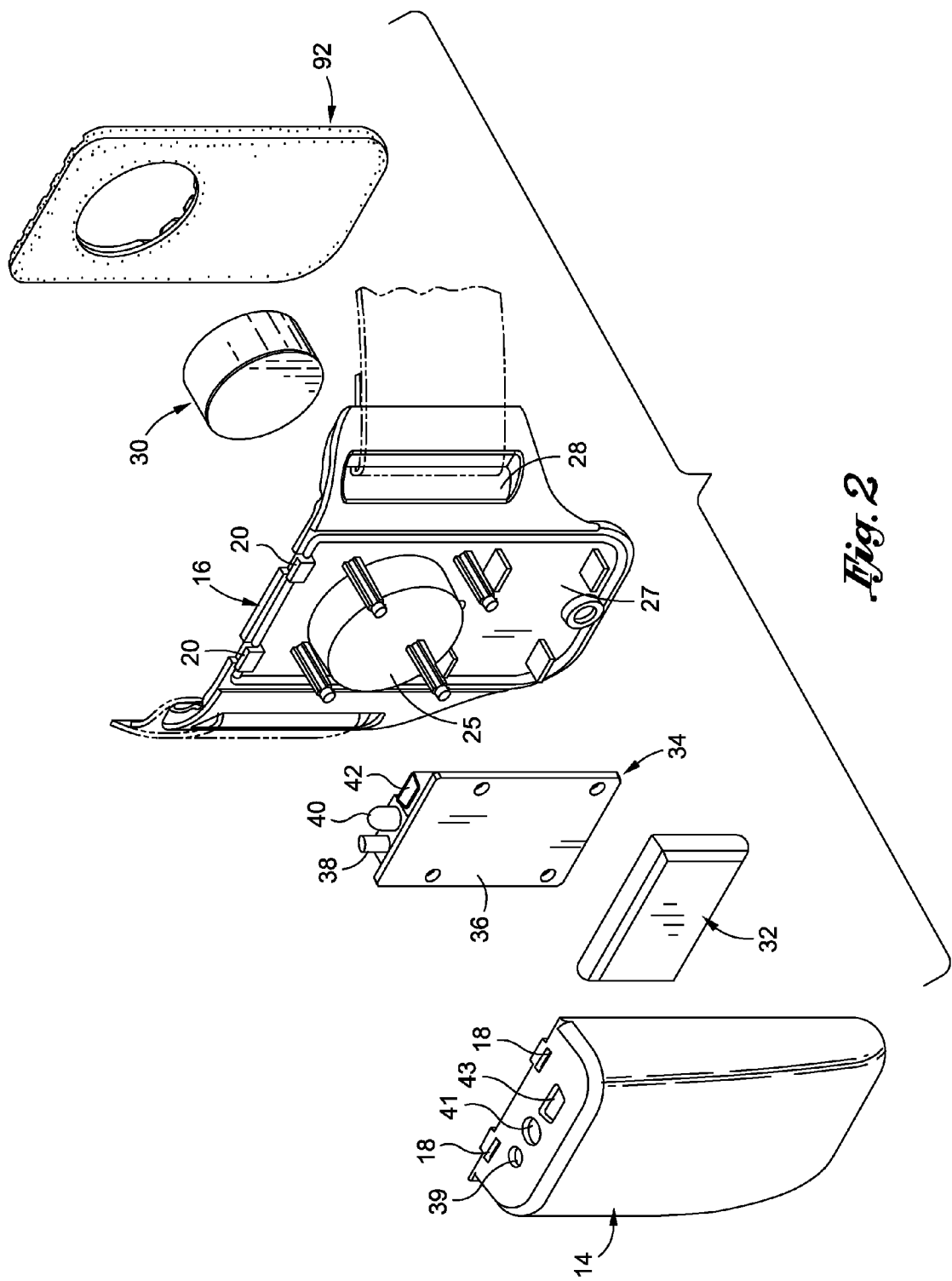
FIG. 2 is an exploded upper perspective view of the medical device.

According to one embodiment, the device 10 includes a housing 12 including a first body 14 (see FIG. 2) and a second body 16 (see FIG. 2). The first and second bodies 14, 16 are connectable to each other to define an enclosure therein. The first and second bodies 14, 16 may have complimentary fastening members to allow for engagement therebetween. In the exemplary embodiment, the first housing body 14 includes a pair of apertures 18 sized to receive respective ones of a pair of engagement tabs 20 formed on the second housing body 20. Those skilled in the art will readily appreciate that the aperture-tab engagement between the first and second bodies 14, 16 shown in the drawings is exemplary in nature only and that other engagement means known in the art may be used to effectuate engagement between the first and second bodies 14, 16.

The first and second bodies 14, 16 may be formed by various manufacturing methods, including injection molding, and may be formed from a bio-compatible material including various plastics (i.e., Kydex, PVCA, etc.) or other bio-compatible materials known by those skilled in the art.

The device 10 further includes a strap 22 connected to the housing 12 for attaching the device 10 in proper position on the patient's leg 24. As noted above, the device 10 is configured to impart a vibrotactile stimulation adjacent the tibia tubercle, and thus, the strap 22 is used to secure the housing 12 on the patient's leg adjacent the tibia tubercle. In the exemplary embodiment, the strap 22 is connected to the second body 16, which includes a pair of slots 26, 28 formed on opposed sides of the housing 12 through which the strap 22 is advanced. The strap 22 may be fixed to one of the slots 26, 28 adjacent one end portion of the strap 22, and selectively adjustable through another one of the slots 26, 28 to allow the strap 22 to be sized to the specific size of the wearer's leg. In particular, the adjustable end may be used to cinch the strap 22 onto the wearer's leg to properly connect the device 10 to the patient. The strap 22 may employ hook and loop fasteners, i.e., VELCRO™, or other mechanical fasteners known by those skilled in the art to secure the strap 22 to the patient's leg. The strap 22 is also configured to allow for easy adjustability to facilitate attachment to the patient, as well as use on various patient sizes.

The device 10 further includes a vibrating element 30 which imparts the vibrotactile stimulation to the patient. The exemplary vibrating element 30 shown in FIG. 2 is a cylindrically shaped element which at least partially resides within a recess formed within the second body 16. In this regard, the second body 16 includes a recess wall 25 which extends from a base wall 27, wherein the recess wall 24 defines the recess within which the vibrating element 30 resides.

The device 10 additionally includes a battery 32 and a control unit 34 for providing power and control to the device 10. The battery 32 and control unit 34 are disposed within the enclosure collectively defined by the first and second bodies 14, 16. The control unit 34 includes a control base plate 36 and a user interface connected to the control base plate 36. The user interface includes a control button 38 and an indicator light 40. The control unit 34 further includes a data and power port 42 for communicating with external resources, such as a remote data transfer unit and a remote power unit, as described in more detail below. When the control unit 34 is placed within the housing 12, the control button 38, indicator light 40, and data and power port 42 are aligned with respective openings 39, 41, 43 formed within the first body 14.

Figure 3:
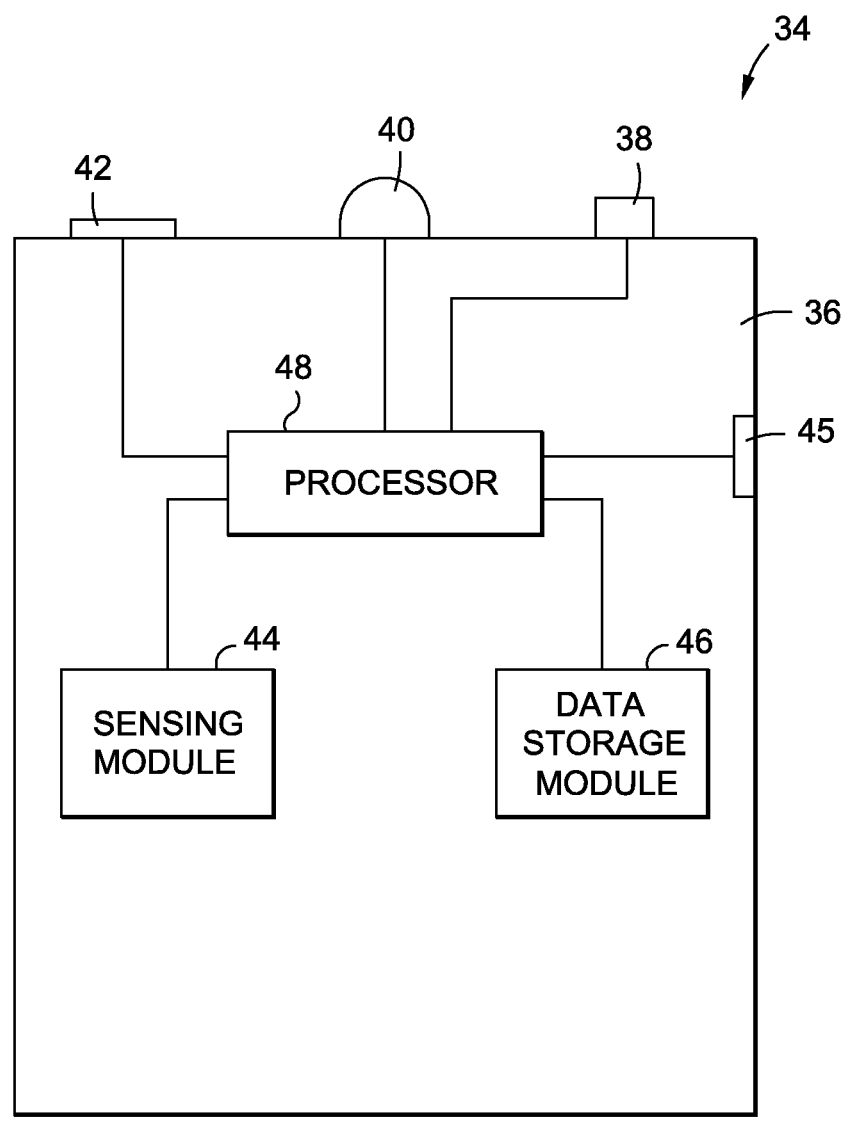
FIG. 3 is a schematic view of a control unit used in the medical device.

Referring now to FIG. 3 there is shown a schematic view of the control unit 34, which includes a sensing module 44, data storage module 46, a processor 48, and control unit port 45. The sensing module 44 is configured to detect leg movements during the patient's gait and communicate that information to the processor 48. The processor 48 processes that information to identify the various stages of the patient's gait during leg movement. The processor 48 is configured to generate an actuation signal to stimulate the patient. The actuation signal is communicated to the vibrating element 30 through the control unit port 45.

According to various embodiments, the sensing module 44 includes a micro-electrical-mechanical systems (MEMS) accelerometer to measure the acceleration/deceleration of the patient's leg during gait. An exemplary sensing module may be capable of measuring +/−2 g on three axes. The sensing module 44 may additionally include a gyro to measure the angular movement of the patient's leg. In one implementation, the gyro is a MEMS gyro configured to measure +/−300°/s about the knee axis.

Those skilled in the art will readily appreciate that the vibrotactile stimulation can be imparted on the patient at various points throughout the patient's gait cycle. The timing of the stimulation may depend on the particular gait cycle of the patient. For instance, the stimulation may differ for a patient who shuffles compared to a patient who does not shuffle. The control unit 34 may have several preprogrammed settings to adapt the operation of the device 10 to conform to the particular gait cycle of the patient.

According to one embodiment, the vibrotactile stimulation is generated when the heel strike portion of the gait is detected. Thus, the control unit 34 detects when the heel strike occurs. Along these lines, the processor 48 includes an algorithm used to determine when the heel strike occurs. In general, the inputs to the algorithm are the motions measured by the sensing module 44, as well as a time input. The output is a signal corresponding to the intensity of the vibration that the vibrating element 30 should produce.

A key feature of the algorithm is that it generates a short pulse of vibration output in response to the patient's foot hitting the ground. The impact is generally detected by comparing a variable which is substantially the vertical accelerometer output to a threshold. In many embodiments, the algorithm distinguishes between foot impacts and other accelerations of the lower leg (such as those that occur when the opposite foot impacts, as well as at other stages during the gait cycle). This distinguishing may be achieved by comparing the rotation rate or rotation amount of the leg to a threshold, and then only responding to an impact which occurs after the rotation threshold has been previously reached.

In one implementation, the gravity vector of the patient's leg is tracked in the two planes. A foot impact is detected as an additional 0.5 g in this plane beyond the gravity vector in the two planes. A heel strike is detected if a foot impact occurs within 200 ms after a rearwards rotation in the knee axis of more than 50°/s.

Specific examples of algorithms which may be used in the device 10 are shown below. It is understood that the following algorithms are exemplary in nature only, and that the present invention is not limited thereto.

Common Bit:

1. Wait for sampling interval, then read and filter inputs from Accerometer in the vertical direction (AccY), forward direction (AccZ) and Gyro in the X plane (GyroX); 2. CombinedAcc=sqrt(AccY*AccY+AccZ*AccZ)−GravityAmount; 3. If GyroX>GXSwingThresh then set CountDown=Interval; 4. If SenseCountDown>0 and GyroX<GXSwingThresh then set swing flag, otherwise clear swing flag; 5. If SenseCountDown>0 then set swing flag GravityAmount may be a fixed value or it may be found during operation from CombinedAcc by applying any of a variety of low pass filters with bandwidths of significantly less than the step frequency, for example about 0.5 Hz CombinedAcc is substantially determined by the vertical acceleration, because in normal gaits, vertical impacts and movements are significantly greater than forward ones.

Algorithm 1

6. If Swing flag is set and CombinedAcc>CombinedAccThreshold then initiate vibrotactile actuator sequence and clear swing flag; 7. repeat from 1.

Once initiated, the vibrotactile actuator sequence generates a 250 Hz output for a duration of 80 ms (could sensibly range from 10-200 ms). For clarity, the means of generating the frequency and timing the duration is not described, but is obvious to anyone skilled in the art.

Algorithm 2

6. If CombinedAcc>AYImpactThresh then EngSum=EngSum+(CombinedAcc−AYImpactThresh); 7. If Swing flag is set and EngSum>MinValBuzz, then set vibrotactile actuator output proportionally to EngSum−MinValBuzz; 8. repeat from 1.

The vibrotactile actuator output algorithm outputs at the most recently assigned intensity for a duration of 80 ms. The swing flag is cleared after this.

Algorithm 3

6. If Swing flag is set then set vibrotactile actuator output proportionally to CombinedAcc−AYImpactThresh; 7. repeat from 1

The vibrotactile actuator output may be proportioned using any of a number of equations. For example: PWMPercentage=100*(X−MinValBuzz)/(MaxValBuzz−MinValBuzz)

In addition to detecting a heel strike, various embodiments of the algorithm may also be capable of detecting other events. For instance, the algorithm may be operative to detect sudden impacts that may be indicative of falls or other potential trauma events to the patient. This detection may be achieved by comparing the accelerometer signals to at least one threshold, and detecting the trauma event when the threshold is exceeded. In other embodiments, the algorithm compares accelerometer signals to at least one threshold, and also compares the accelerometer signals from two axes to determine if the orientation of the device has substantially changed. For example, the algorithm may detect if the patient's leg has changed from a substantially vertical orientation to a substantially horizontal orientation. If a fall or other traumatic event is detected, the device 10 may cease normal operation and communicate an emergency alert signal (i.e., an audible signal such as a beep/buzzer or a wireless communication signal to an emergency response team).

Figure 4:
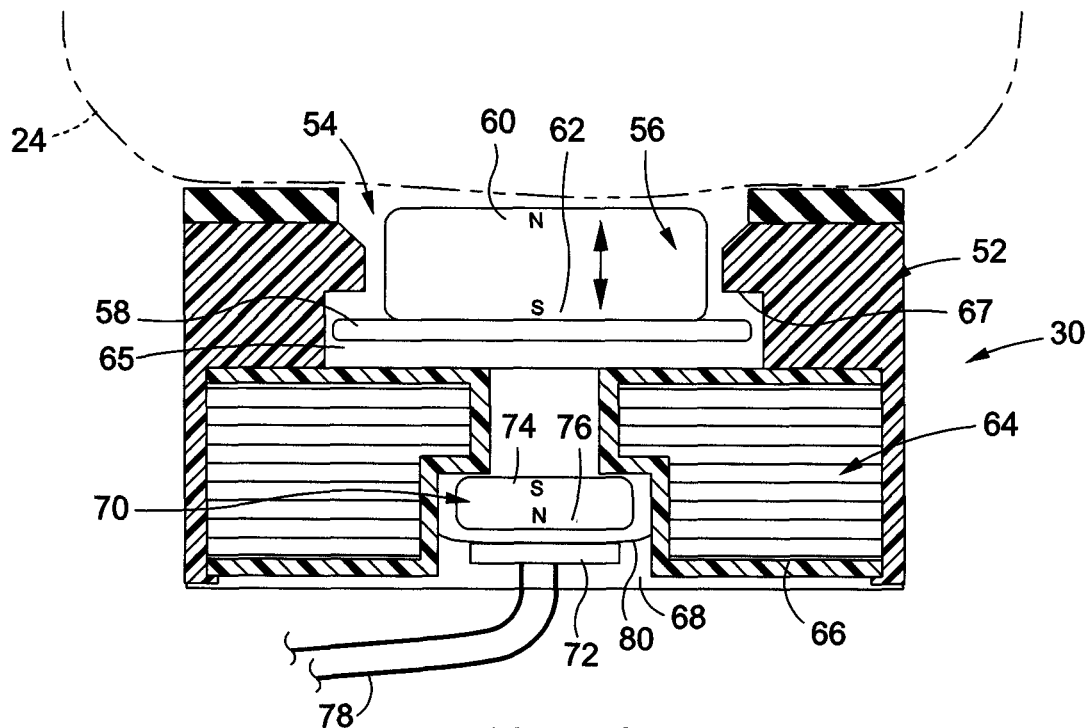
FIG. 4 is an embodiment of a vibrating element used in the medical device to impart a vibrotactile stimulation on the patient.

As indicated above, in the preferred embodiment under normal operating conditions, when a heel strike is detected, the processor 48 is configured to generate an actuation signal to actuate the vibrating element 30. Referring now specifically to FIG. 4, there is shown a cross sectional view of one embodiment of the vibrating element 30, which includes a housing body 52 and a moveable element 54 disposed within the housing body 52 and moveable relative thereto. The moveable element 54 includes a primary magnet 56 and a flange element 58 connected to the primary magnet 56. The primary magnet 56 includes a distal end portion 60 and an opposing proximal end portion 62, with the flange element 58 being connected to the proximal end portion 62. The flange element 58 is disposed within a flange opening 65 located within the housing body 52.

The vibrating element 30 further includes a primary coil 64 located within a protective coil covering 66. The coil covering 66 defines a toroidal shape that includes an inner opening 68. A secondary magnet 70 and an interconnect board 72 are disposed within the inner opening 68. The secondary magnet 70 includes a first end portion 74 and an opposing second end portion 76. The interconnect board 72 includes wire leads 78 which connect to the control unit 34, and wire leads 80 which extend to the primary coil 64. Therefore, power may be communicated from the control unit 34, to the interconnect board 72, and then to the primary coil 64.

The vibrating element 30 generates the vibrotactile force as a result of the magnetic attraction/repulsion of the primary magnet 56 relative to the secondary magnet 70. In this regard, the polarity of the secondary magnet 70 may be switched by alternating the current through the primary coil 64. Thus, if the primary coil 64 is supplied with alternating current (AC), the current is constantly changing directions in the primary coil 64, and thereby changing the polarity of the secondary magnet 70.

The moveable element 54 is moveable relative to the housing body 52 between a patient engagement position, wherein the distal end portion 60 engages with the patient's leg 24, and a retracted position, wherein the distal end portion 60 is spaced from the patient's leg 24. When the moveable element 54 is in the patient engagement position, the flange element 58 may engage with a contact surface 67 of the housing body 52 to limit further movement away from the secondary magnet 70 and toward the patient's leg 24. Furthermore, when the moveable element 54 is in the retracted position, the flange element 58 may engage with the coil covering 66 to stop further movement of the moveable element 54 toward the secondary magnet 70.

According to one embodiment, the primary magnet 56 defines a mass that is low enough such that the magnetic interaction can generate enough force to overcome the inertia of the primary magnet 56 to create sufficient movement of the primary magnet 56 to stimulate the patient's skin.

The vibrating element 30 may include a spring which interfaces with the primary magnet 56. The spring may include a spring constant such that the mass of the primary magnet 56 will naturally mechanically resonate at around the intended vibration frequency.

Figure 5:
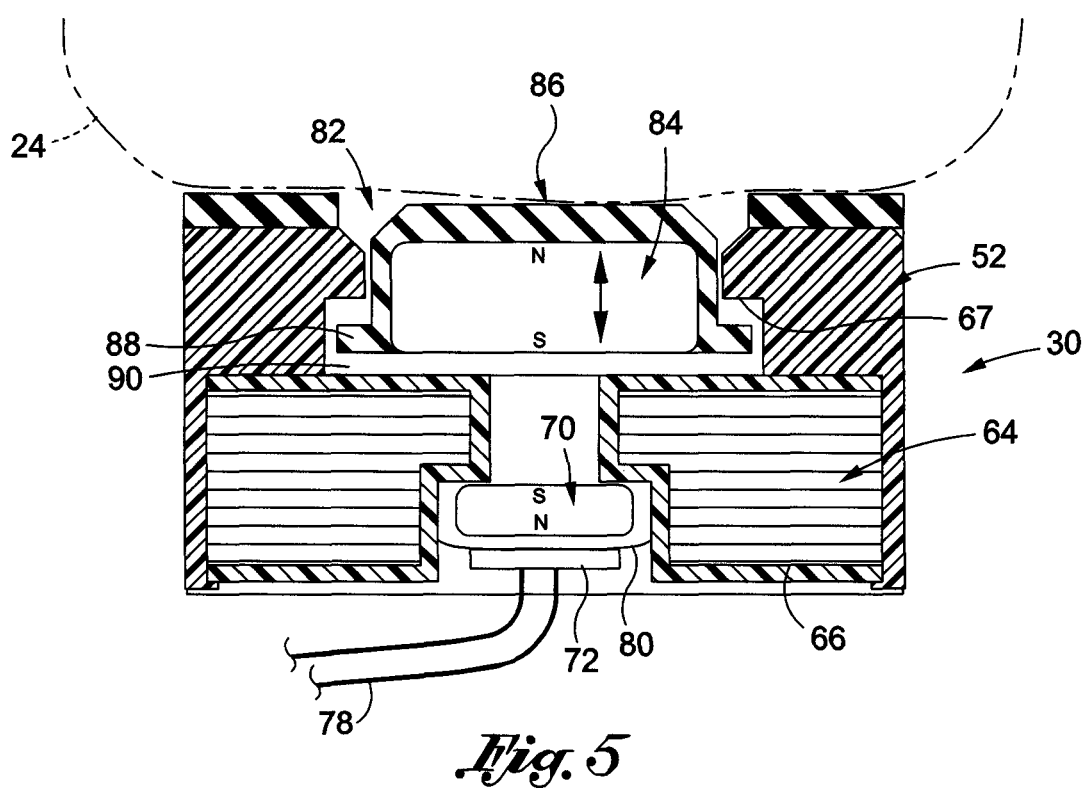
FIG. 5 is a second embodiment of the vibrating element used in the medical device.

Referring now specifically to FIG. 5, there is shown another embodiment of the vibrating element 30, with the primary difference relating to the moveable element. In particular, the moveable element 82 shown in FIG. 5 includes a primary magnet 84 with a molded layer 86 connected thereto. The molded layer 86 at least partially encapsulates the primary magnet 84 and forms a flange 88 which resides within a pocket 90 formed within the vibrating element body. The flange 88 performs the same functionality as the flange element 58 described above in relation to the moveable element 54.

The vibrotactile stimulation imparted by the vibrating element 30 re-establishes the sensorimotor loop by providing the patient with a secondary signal to healthy nerves around the knee. The signal alerts the patient that the patient's heel just struck the ground. The vibrotactile stimulation is preferably applied to the pacinian corpuscles around the knee. These corpuscles are typically not affected by peripheral neuropathy and have a dedicated pathway to the central nervous system. The patient's central nervous system incorporates the new signal and the patient's motor system responds as if there is no loss of sensation in the foot, and thus, returns to its normal pattern of gait.

As indicated above, the device 10 may include a data storage module 46 for storing data related to usage of the device 10. For instance, the data storage module 46 may be configured to record the number of heel strikes detected by the device 10. In some embodiments, the data storage module 46 may record data that indicates patient time of use, patterns of use, durations of use, and frequency of use for later access. For example, the data storage module 46 may be configured to store data at preset time intervals. The time intervals may range from less than one minute to greater than one day. However, in a preferred embodiment, the time interval for data storage is approximately 10 to 15 minutes.

The data recorded at the end of each time interval may indicate the operational status of the device 10, as well as the number of steps detected within that interval. In some embodiments, the stored data may also indicate whether a trauma event was detected within that interval. The operational status may include whether the device 10 is in STANDBY mode or not, or whether the device 10 is on the battery charger.

In some embodiments the device 10 stores a time stamp associated with each step into a storage memory. The time stamp may have a resolution of less than 20 milliseconds and may be recorded in a rotating buffer in Random Access Memory. According to one implementation, the rotating buffer stores 256 timestamps. This timing data is used to assess variabilities in stride times (for example, in a controlled environment).

The patient or medical professional may be able to download the recorded data via the data and power port 42. For instance, the patient or medical professional may use an external computing device (i.e., PC, laptop, smart phone, tablet computer, PDA, etc.) and request data using a Universal Serial Bus port, i.e., the data and power port 42. The data may be presented to the user on the computer's screen. The computer may also be configured to transfer the data to a database or other such medical record keeping system. The computer may further be configured to perform additional analysis on the data recorded by the device 10. The computer may additionally be configured to present the data or the results of further analysis of the recorded data in a graphical way. Once the data is downloaded from the device 10, the heel count may be reset to zero and any other data may be deleted or reset.

Power may be supplied to the device 10 from the battery 32. According to one embodiment, the battery 32 is a 1.5 Whr Lithium Ion Polymer rechargeable battery. A typically rating of a battery is sufficient for 17000 steps or 36 hours of walking time. This is expected to last at least for 6 days of use. The battery 32 may have a maximum capacity loss of 30% over 500 charge/discharge cycles, and thus may meet the foregoing requirements for at least 5 years.

During charging the device 10 may be configured to draw up to 100 mA from the connected power source during charging. The device 10 will finish charging when the battery 32 is full, and will not overcharge the battery 32 if left continuously connected. The battery 32 may fully charge in less than 10 hours.

The data and power port 42 may be configured for use with a plug connectable cable to deliver power to the device 10 for recharging the battery, and for establishing a communication pathway between the device 10 and a remote computing device. The remote computing device may include a desktop computer, laptop computer, tablet computer, personal digital assistant (PDA), smart phone or other computing device known by those skilled in the art. The plug connectable cable may include a USB plug to connect to a USB port on the remote computer device, although other configurations of plugs may also be used.

Furthermore, it is also contemplated that the device 10 may wireless sly communicate information. For instance, the device 10 may be configured to upload data to a smart phone, tablet computer, laptop computer, desktop computer, or other remote computing device. Along these lines, the wireless communication may occur via various wireless communication protocols known in the art, including Bluetooth™, infrared, WiFi, RF, or other wireless communication means.

The control button 38 is a push button positioned on the device 10 such that it is easy to access when worn by the patient. In the exemplary embodiment shown in FIGS. 1 and 2, the control button 38 is extends through the upwardly facing surface of the housing 12. The control button 38 may be a push button which toggles the device 10 between an OFF state and an ON state.

It is also contemplated that various embodiments of the device 10 may include a STANDBY state. In a battery powered device, using power unnecessarily is preferably avoided. The device 10 is typically used on patients who spend most of their time in a resting state, i.e., not walking. When the patient is not walking, it is desirable that the device 10 is turned into the OFF state; however, it is tedious to require the patient to turn the device 10 ON or OFF as needed. Therefore, the device 10 includes a STANDBY state which conserves power when the patient is not walking. More specifically, when the device 10 is not in use, the control unit 34 will cause the device 10 to enter a low power mode, wherein some or all of the sensors are powered off or placed in a low power mode of operation. The control unit 34 will utilize the remaining sensors, or periodically re-enable the disabled sensors at intervals much longer than the operational sampling rates, to determine when conditions for the STANDBY state are no longer present and full power should resume, i.e., transition from the STANDBY state to the ON state. For instance, the STANDBY state may be maintained while the direction of the gravity vector measured by the accelerometer is further than a threshold from the normal direction, such as when the patient is reclined or the device 10 is not being worn by the patient. Furthermore, if not foot impacts have been detected for some interval, the STANDBY state may be maintained while no rotations or impacts above set thresholds are measured, such as when the patient is stationary or when the device 10 is not worn by the patient.

The indicator light 40 may be positioned on the device 10 to allow the patient to see the light 40 during usage of the device 10. According to one embodiment, the indicator light is a bi-color LED extending through the upward surface of the housing. The LED may pulse green when the device 10 is ON and slowly pulse red when the battery is below 30% remaining capacity. The LED may rapidly pulse red when the battery capacity is so low that the device 10 is no longer functioning. A solid red LED indicates that the device 10 is charging, while a solid green LED indicates that the battery is completely charged.

The device 10 may be configured to be worn with comfort. Along these lines, the device includes a padded layer 92 connected to the housing 12, which provides a comfortable interface with the device 10. The padded layer 92 may form and compress to the patient physiology to secure the device 10 in proper leg alignment. Furthermore, various embodiments of the device 10 define a compact and discrete physical form factor which allows it to be easily worn beneath slacks and skirts. The housing may also be ergonomic, wherein the attaching areas of the housing flex upon strap 22 tightening to comply and contour with the patient's physiology.

The device 10 provides several benefits to the wearer, including improving the patient's gait, increased mobility, strength, and endurance, decreased energy expenditure, prevention, retardation, and/or reversal of muscle atrophy, and maintained or increased joint range of motion. Further benefits may include reduced incidence of injury, increased circulation, muscle re-education, maintained or increased bone density, and strengthened damaged central nervous system pathways and muscle/spinal circuits.

It addition to the foregoing, it is contemplated that various implementations of the device 10 may be specifically adapted for use while driving. Polyneuropathy may result in pain, numbness, and weakness, which may in turn affect one's driving ability. Neuropathy patients are involved in traffic accidents at a greater rate, and state that their condition affects their driving and often change their driving habits after developing neuropathy. Independently, elevated levels of pain, motor weakness, and ambulation difficulty met statistical significance for increased MVA frequency.

In some embodiments of the device 10, the device 10 incorporates sensors on the gas and brake pedals of a motor vehicle. The sensors may be pressure sensors fitted to the pedals, or sensors that measure the location of the pedals as they move. In some embodiments, the vehicle's existing sensors are used. The device 10 will produced increased intensity of vibration based on the amount of pressure on the pedal.

In some embodiments, the device 10 will produce a different vibration frequency for the gas and brake pedal. In some embodiments, the device will produce vibration using separate actuators fitted in different locations to the patient for the gas and brake pedal. In other embodiments, the signals from the pedals are transmitted wirelessly to the device, either from the electronics related to the pedal or from the vehicle's on-board computer.

Additional modifications and improvements of the present invention may also be apparent to those of ordinary skill in the art. Thus, the particular combination of components and steps described and illustrated herein is intended to represent only certain embodiments of the present invention, and is not intended to serve as limitations of alternative devices and methods within the spirit and scope of the invention.

What is claimed is:

1. A medical device for restoring gait for a patient, the medical device comprising:
    a housing configured to be wearable on a patient's leg;
    a vibrating element connected to the housing and configured to impart a vibrotactile force upon the patient's leg; and
    a control unit connected to the housing and in operative communication with the vibrating element;
    the control unit being configured to:
        measure a leg rotation amount about a rotation axis and an axial leg acceleration amount along an acceleration axis during the patient's gait;
        compare the leg rotation amount and axial leg acceleration amount to respective thresholds; and
        generate an actuation signal based on a combined assessment of the leg rotation amount, axial leg acceleration amount, and a timing threshold associated with a specified period of time, the actuation signal being generated to actuate the vibrating element when the leg rotation amount and leg acceleration amount both meet their respective thresholds within the timing threshold, the actuation signal not being generated when either one of the leg rotation amount and the axial leg acceleration amount do not meet their respective thresholds.

2. The medical device recited in claim 1, wherein the housing is configured to be positionable adjacent the tibia tubercle of the patient's leg.

3. The medical device recited in claim 1, wherein the vibrating element includes a permanent magnet and a winding, and a flange extending radially outward from the permanent magnet, the flange being configured to maintain the permanent magnet within a cavity formed within the housing.

4. The medical device recited in claim 1, wherein the vibrating element is configured to impart a vibrating force at approximately 250 Hz.

5. The medical device recited in claim 4, wherein the vibrating element imparts the vibrating force for approximately 10-200 ms.

6. The medical device recited in claim 5, wherein the vibrating element imparts the vibrating force for approximately 80 ms.

7. The medical device recited in claim 1, wherein the vibrating element is configured to define a rise time of approximately 10-40 ms.

8. The medical device recited in claim 1, wherein the control unit includes an accelerometer configured to detect acceleration along 1-3 axes.

9. The medical device recited in claim 1, wherein the control unit is configured to detect leg movements according to one of a plurality of pre-programmed gait settings.

10. The medical device recited in claim 9, wherein the control unit is configured to allow a user to selectively switch between the plurality of pre-programmed gait settings.

11. The medical device recited in claim 1, further comprising a strap connected to the housing, the strap being configured to connect the housing to the patient's leg.

12. The medical device recited in claim 1, further comprising a battery in operative communication with the control unit.

13. The medical device recited in claim 12, wherein the battery is rechargeable.

14. The medical device recited in claim 1, wherein the control unit is further configured to generate the actuation signal in response to the prescribed combination of detected leg rotation and leg impact within prescribed timing parameters.

15. A medical device for aiding gait restoration in a patient having a gait cycle, the medical device comprising:
   a housing wearable on the leg of the patient adjacent the tibia tubercle;
   a sensing module connected to the housing and configured to:
      sense both rotational movement of the patient's leg and axial acceleration of the patient's leg;
      identify when the patient's leg is in a prescribed position based on a combined assessment of a measured leg rotation amount, a measured axial leg acceleration amount, with the leg rotation amount and axial leg acceleration amount occurring within a prescribed time period; and
      generate a stimulation signal when a sensed position of the patient's leg is in the prescribed position within the prescribed time period; and
   a stimulator connected to the housing and in operative communication with the sensing module to receive the stimulation signal therefrom, the stimulator being configured to impart a stimulating force on the patient's leg in response to receipt of the stimulation signal.

16. The medical device recited in claim 15, wherein the stimulator is configured to vibrate relative to the housing to impart the stimulating force on the patient's leg.

17. The medical device recited in claim 15, wherein the sensing module is configured to detect leg movements according to one of a plurality of pre-programmed gait settings.

18. The medical device recited in claim 15, wherein the sensing module is further configured to generate the stimulation signal in response to the prescribed combination of detected leg rotation and leg impact within prescribed timing parameters.

19. A medical device for restoring gait for a patient, the medical device comprising:
   a housing configured to be wearable on a patient's leg adjacent the tibial tubercle;
   a vibrating element connected to the housing and configured to impart a vibrotactile force upon the tibal tubercle, the vibrating element including a magnet and a flange coupled to the magnet, the flange being configured to maintain the magnet within a cavity formed within the housing; and
   a control unit connected to the housing and in operative communication with the vibrating element;
   the control unit being configured to: measure a leg rotation amount about a rotation axis and an axial leg acceleration amount along an acceleration axis during the patient's gait; compare the leg rotation amount and axial leg acceleration amount to respective thresholds; and generate an actuation signal based on a combined assessment of the leg rotation amount, axial leg acceleration amount, and a timing threshold associated with a specified period of time, the actuation signal being generated to actuate the vibrating element when the leg rotation amount and leg acceleration amount both meet their respective thresholds within the timing threshold.

20. The medical device recited in claim 19, wherein the control unit is further configured to generate an emergency response signal in response to the detected leg movements being associated with a defined traumatic event.

* * * * *